US00PP20505P2

(12) United States Plant Patent
Kitamura

(10) Patent No.: US PP20,505 P2
(45) Date of Patent: Nov. 24, 2009

(54) *CALIBRACHOA* PLANT NAMED 'SUNBELRIKUBU'

(50) Latin Name: ***Calibrachoa* sp.**
Varietal Denomination: Sunbelrikubu

(75) Inventor: Kenichi Kitamura, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 198 days.

(21) Appl. No.: 11/903,790

(22) Filed: Sep. 25, 2007

(51) Int. Cl.
*A01H 5/00* (2006.01)

(52) U.S. Cl. ..... Plt./413

(58) Field of Classification Search ..... Plt./413, Plt./356

See application file for complete search history.

*Primary Examiner*—Howard J Locker
(74) *Attorney, Agent, or Firm*—C. A. Whealy

(57) ABSTRACT

A new and distinct cultivar of *Calibrachoa* plant named 'Sunbelrikubu', characterized by its outwardly spreading and trailing plant habit; vigorous growth habit; freely branching and flowering plant habit; long flowering period; and purple-colored flowers.

1 Drawing Sheet

Botanical designation: *Calibrachoa* sp.
Cultivar denomination: 'Sunbelrikubu'.

BACKGROUND OF THE INVENTION

The present invention relates to a new and distinct cultivar of *Calibrachoa,* botanically known as *Calibrachoa* sp. and hereinafter referred to by the name 'Sunbelrikubu'.

The new *Calibrachoa* is a product of a planned breeding program conducted by the Inventor in Higashiomi, Shiga, Japan. The objective of the breeding program is to develop new uniform *Calibrachoa* cultivars with attractive and unique flower coloration.

The new *Calibrachoa* is a naturally-occurring branch mutation of a proprietary selection of *Calibrachoa* sp. identified as code number CRP4, not patented. The new *Calibrachoa* was discovered and selected by the Inventor from within a population of plants of the parent selection in a controlled environment in Higashiomi, Shiga, Japan in May, 2004.

Asexual reproduction ofthe new *Calibrachoa* by terminal cuttings in a controlled environment in Higashiomi, Shiga, Japan since September, 2005, has shown that the unique features of this new *Calibrachoa* are stable and reproduced true to type in successive generations.

SUMMARY OF THE INVENTION

The cultivar Sunbelrikubu has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunbelrikubu'. These characteristics in combination distinguish 'Sunbelrikubu' as a new and distinct cultivar of *Calibrachoa:*

1. Outwardly spreading and trailing plant habit.
2. Vigorous growth habit.
3. Freely branching and flowering plant habit.
4. Long flowering period.
5. Purple-colored flowers.

Plants of the new *Calibrachoa* can be compared to plants of the parent selection. Plants of the new *Calibrachoa* differ from plants of the parent selection in the following characteristics:

1. Flower petals of plants of the new *Calibrachoa* are not as rounded as flower petals of plants of the parent selection.
2. Plants of the new *Calibrachoa* and the parent selection differ in flower color.

Plants of the new *Calibrachoa* can also be compared to plants of the cultivar Sunbelkubu, disclosed in U.S. Plant Pat. No. 10,279. In side-by-side comparisons conducted in Higashiomi, Shiga, Japan, plants of the new *Calibrachoa* and the cultivar Sunbelkubu differed in the following characteristics:

1. Plants of the new *Calibrachoa* were taller than plants of the cultivar Sunbelkubu.
2. Leaves of plants of the new *Calibrachoa* were lanceolate in shape whereas leaves of plants of the cultivar Sunbelkubu were ovate in shape.
3. Plants of the new *Calibrachoa* had larger flowers than plants of the cultivar Sunbelkubu.
4. Plants of the new *Calibrachoa* and the cultivar Sunbelkubu differed in flower color.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbelrikubu' grown in a container.

The photograph at the bottom of the sheet comprises a close-up view of typical flowers of 'Sunbelrikubu'.

DETAILED BOTANICAL DESCRIPTION

The aforementioned photographs and following observations, measurements and values describe plants grown in Higashiomi, Shiga, Japan, under commercial practice during the late spring and summer in a polyethylene-covered greenhouse. During the production of the plants, day temperatures averaged 23° C. and night temperatures averaged 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Calibrachoa* sp. cultivar Sunbelrikubu.

Parentage: Naturally-occurring branch mutation of a proprietary selection of *Calibrachoa* sp. identified as code number CRP4, not patented.

Propagation:

*Type.*—By terminal cuttings.

*Time to initiate roots.*—About one week at 20° C. to 25° C.

*Time to produce a rooted young plant.*—About three weeks at 20° C. to 25° C.

*Root description.*—Fine, fibrous; light brown in color.

*Rooting habit.*—Freely branching.

Plant description:

*Plant and growth habit.*—Outwardly spreading and trailing plant habit. Freely branching with lateral branches potentially forming at every node; pinching enhances lateral branch development. Vigorous growth habit.

*Plant height.*—About 9.4 cm.

*Plant diameter.*—About 44.4 cm.

Lateral branch description:

*Length.*—About 20.4 cm.

*Diameter.*—About 1.1 mm.

*Internode length.*—About 4 mm.

*Strength.*—Strong.

*Aspect.*—Decumbent.

*Texture.*—Pubescent.

*Color.*—144A.

Foliage description:

*Arrangement.*—Alternate, simple.

*Length.*—About 3.1 cm.

*Width.*—About 1 cm.

*Shape.*—Lanceolate.

*Apex.*—Obtuse.

*Base.*—Cuneate.

*Margin.*—Entire.

*Texture, upper and lower surfaces.*—Sparsely pubescent.

*Venation pattern.*—Pinnate; reticulate.

*Color.*—Developing and fully expanded foliage, upper surface: 137A; venation, 145B. Developing and fully expanded foliage, lower surface: 137C; venation, 145B.

*Petiole.*—Length: About 4.6 mm. Diameter: About 0.6 mm. Texture, upper and lower surfaces: Sparsely pubescent. Color, upper and lower surfaces: 145B.

Flower description:

*Flower arrangement and habit.*—Single salverform flowers arising from upper leaf axils. Freely flowering habit with usually about two open flowers per lateral branch. Flowers not persistent. Flowers face upright or outwardly. Flowers not fragrant.

*Natural flowering season.*—Plants of the new *Calibrachoa* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant.

*Flower diameter.*—About 3.8 cm.

*Flower length (depth).*—About 2.6 cm.

*Throat diameter.*—About 7.2 mm.

*Tube length.*—About 1.6 cm.

*Tube diameter.*—About 1.5 mm.

*Flower bud.*—Shape: Cylindrical. Length: About 2.1 cm. Diameter: About 4.1 mm. Color: 83C.

*Corolla.*—Arrangement: Five petals fused at the base and opening into a flared trumpet. Petal length from throat: About 1.4 cm. Petal width: About 1.7 cm. Petal shape: Spatulate. Petal apex: Rounded with truncate tendencies. Petal margin: Entire. Petal texture, upper and lower surfaces: Smooth, glabrous; velvety. Color: Petal, when opening, upper surface: Close to 83A. Petal, when opening, lower surface: Close to N82C. Petal, fully opened, upper surface: Close to 83B; color becoming closer to 83C with development. Petal, fully opened, lower surface: Close to N82C; venation, N79A. Throat: 7A. Tube: 8B.

*Calyx.*—Arrangement: One star-shaped calyx tube with five sepals fused at the base per flower. Sepal length: About 1.3 cm. Sepal width: About 2.2 mm. Sepal shape: Lanceolate. Sepal apex: Acute. Sepal margin: Entire. Sepal texture, upper and lower surfaces: Pubescent. Color, immature and mature, upper surface: 137C. Color, immature and mature, lower surface: 144A.

*Peduncles.*—Length: About 2.5 cm. Diameter: About 0.7 mm. Angle: Upright to outwardly. Strength: Strong. Texture: Smooth. Color: 144A.

*Reproductive organs.*—Stamens: Quantity/arrangement: Five per flower. Stamen length: About 7 mm to 12 mm. Anther shape: Ellipsoidal. Anther size: About 1 mm by 1 mm. Anther color: 8A. Pollen amount: Moderate. Pollen color: 8A. Pistils: Quantity: One per flower. Pistil length: About 1 cm. Style color: 144C. Stigma shape: Transversely ellipsoidal. Stigma color: 144A. Ovary color: 144A.

Seed/fruit:

Seed and fruit development have not been observed on plants of the new *Calibrachoa*.

Temperature tolerance: Plants of the new *Calibrachoa* have been observed to tolerate temperatures from about 5° C. to about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Sunbelrikubu' as illustrated and described.

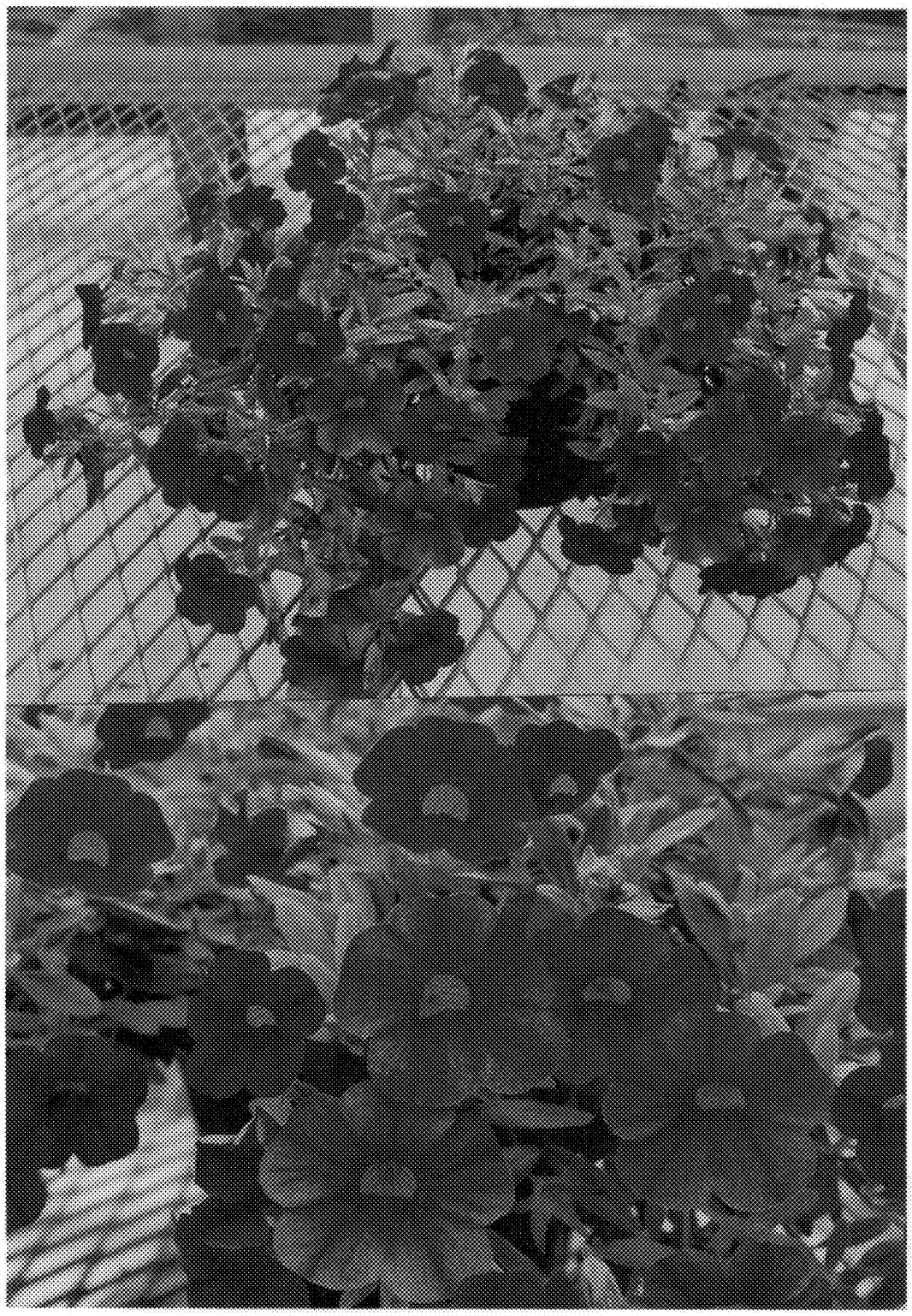

* * * * *